(12) United States Patent
Brown et al.

(10) Patent No.: US 7,629,498 B2
(45) Date of Patent: Dec. 8, 2009

(54) PROCESS OF MANUFACTURING PARA-XYLENE

(75) Inventors: Stephen Harold Brown, Bernardsville, NJ (US); John Scott Buchanan, Lambertville, NJ (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 298 days.

(21) Appl. No.: 11/823,584

(22) Filed: Jun. 28, 2007

(65) Prior Publication Data

US 2009/0000988 A1    Jan. 1, 2009

(51) Int. Cl.
*C07C 2/66* (2006.01)
(52) U.S. Cl. .................................. 585/467; 585/323
(58) Field of Classification Search ................. 585/467, 585/323
See application file for complete search history.

(56) References Cited

U.S. PATENT DOCUMENTS

| | | | |
|---|---|---|---|
| 4,101,595 A | 7/1978 | Chen et al. | |
| 6,046,372 A | 4/2000 | Brown et al. | |
| 6,680,418 B2 | 1/2004 | Brown | |
| 7,119,239 B2 | 10/2006 | Johnson et al. | |
| 7,176,339 B2 | 2/2007 | Iaccino et al. | |
| 7,186,873 B2 | 3/2007 | Feng et al. | |
| 2004/0158111 A1 | 8/2004 | Johnson et al. | |
| 2005/0075524 A1 | 4/2005 | Feng et al. | |

FOREIGN PATENT DOCUMENTS

WO          00/69796          11/2000

OTHER PUBLICATIONS

Yashima et al., "Alkylation on Synthetic Zeolites, I. Alkylation of Toluene with Methanol", Journal of Catalysis, 16, (1970), pp. 273-280.

*Primary Examiner*—Thuan Dinh Dang

(57) ABSTRACT

This disclosure relates to a process of manufacturing para-xylene, comprising (a) contacting a pygas feedstock and methylating agent with a catalyst under reaction conditions to produce a product having para-xylene, wherein the product has higher para-xylene content than the para-xylene content of the pygas feedstock; and (b) separating the para-xylene from the product of the step (a), wherein the catalyst comprises a molecular sieve having a Diffusion Parameter for 2,2-dimethylbutane of about 0.1-15 $\sec^{-1}$ when measured at a temperature of 120° C. and a 2,2-dimethylbutane pressure of 8 kPa-a and the pygas comprises from about 1 to about 65 wt % benzene and from about 5 to 35 wt % toluene.

29 Claims, 3 Drawing Sheets

PROCESS OF MANUFACTURING PARA-XYLENE

FIELD OF THE INVENTION

This disclosure relates to a method of making para-xylene, optionally co-production of light olefins, from pyrolysis gasoline feedstock. In particular, this disclosure relates to method of making para-xylene, optionally co-production of light olefins, from a crude or resid-containing fraction thereof.

BACKGROUND OF THE INVENTION

Of the xylene isomers, para-xylene (PX) is of particular value since it is useful in the manufacture of terephthalic acid which is an intermediate in the manufacture of synthetic fibers. Para-Xylene is presently produced almost exclusively from naphtha by catalytic reforming process. The aromatics produced are used as feedstock to aromatics plants. Aromatics plants purify toluene and mixed xylenes. Purified toluene may be selectively or non-selectively disproportionated to produce para-xylene and benzene. Para-xylene may also be produced from mixed xylenes by isomerization/separations loop.

One known method for producing xylenes involves the alkylation of toluene with methanol over a solid acid catalyst. Thus the alkylation of toluene with methanol over cation-exchanged zeolite Y has been described by Yashima et al. in the Journal of Catalysis 16, 273-280 (1970). These workers reported selective production of para-xylene over the approximate temperature range of 200 to 275° C., with the maximum yield of para-xylene in the mixture of xylenes, i.e. about 50 wt % of the xylene product mixture, being observed at 225° C. Higher temperatures were reported to result in an increase in the yield of meta-xylene and a decrease in production of para and ortho-xylenes.

U.S. Pat. Nos. 7,119,239 and 7,176,339 disclose a process for the production of xylenes from reformate. The process is carried out by methylating under conditions effective for the methylation, the benzene/toluene present in the reformate outside the reforming loop, to produce a resulting product having a higher xylenes content than the reformate. Greater than equilibrium amounts of para-xylene can be produced by the process. U.S. Pat. No. 7,186,873 discloses process for the production of xylenes from reformate by reactive distillation. The process is carried out by methylating the benzene/toluene present in the reformate in a reactive distillation zone and under reactive distillation conditions to produce a resulting product having a higher xylenes content than the reformate. Greater than equilibrium amounts of para-xylene can be produced by the process.

As far as the present inventor is aware, it has previously not been suggested to methylate a pyrolysis gasoline (pygas), to manufacturing para-xylene nor has been suggested to integrate a catalytic system comprising a steam cracker and a methylation unit to produce para-xylene, and optionally co-produce light olefins. There is no prior art disclosing the production of para-xylene from resid and methylating agent feedstocks by any means. There is no prior art teaching the use of methylation technology to convert ethylbenzene to para-xylene and ethylene.

U.S. Pat. No. 6,046,372 discloses a process for converting methanol and/or dimethyl ether to a product containing $C_2$ to $C_4$ olefins which comprises the step of contacting a feed which contains methanol and/or dimethyl ether with a catalyst comprising a porous crystalline material, said contacting step being conducted in the presence of an aromatic compound under conversion conditions including a temperature of 350° C. to 480° C. and a methanol partial pressure in excess of 10 psia (70 kPa), said porous crystalline material having a pore size greater than the critical diameter of the aromatic compound and the aromatic compound being capable of alkylation by the methanol and/or dimethyl ether under said conversion conditions.

U.S. Pat. No. 6,680,418 discloses a process for converting methanol and/or dimethyl ether to a product containing $C_2$ to $C_4$ olefins, which comprises the step of contacting a reaction mixture containing methanol and/or dimethyl ether and at least 10 wt % of a polymethylbenzene component selected from trimethylbenzenes, tetramethylbenzenes and mixtures thereof with a catalyst comprising a porous crystalline material. The contacting step is conducted under conversion conditions including a temperature of about 250° C. to about 500° C. and a methanol and/or dimethyl ether partial pressure of about 5 to about 250 psia (35 to 1725 kPa). The porous crystalline material used in the catalyst has a pore size greater than the critical diameter of the aromatic compound and a Diffusion Parameter for 2,2-dimethylbutane of at least 500 $sec^{-1}$ when measured at a temperature of 120° C. and a 2,2-dimethylbutane pressure of 60 torr (8 kPa).

All methylation processes use relatively pure toluene, mixtures of toluene and benzene, or reformate as feedstock for manufacturing xylene, preferably para-xylene. The sources of toluene/benzene feedstock for the methylation process may be reformate or pygas. However, to the best knowledge of the inventor, there is no disclosure of using pygas as the aromatic feedstock for the methylation process. It is well known to a person of ordinary skill that pygas contains large amount of non-aromatics, some olefinic hydrocarbons, and a high ethylbenzene content in the $C_8$ aromatics. Both non-aromatics and olefinic hydrocarbons are known for catalyst deactivation and aging. Ethylbenzene is known as a bad feedstock for para-xylene production. Furthermore, there is no disclosure using pygas without extraction as the aromatic feedstock for the methylation process. Even more, there is no disclosure using pygas obtained from steam cracking a hydrocarbon feedstock made with hydroprocessed resid with/without extraction as the aromatic feedstock for the methylation process.

There is, therefore, a need to develop a technology to produce para-xylene in high yield from pygas feedstock. Another technical challenge related to use of pygas feedstock for para-xylene production is rapid catalyst deactivation because the pygas feedstock contains certain amount of non-aromatics which may deactivate the catalyst. Therefore the pygas feedstock normally is subjected to an extraction process to remove most of the non-aromatics before further processing. However, the extraction process is expensive and capital intensive. There is also a need to produce aromatic products from pygas without extraction.

We surprisingly discovered a process of manufacturing PX, optionally co-manufacturing light olefins, from a pygas feedstock by methylating the pygas with a methylating agent using a molecular sieve catalyst. Furthermore, the para-xylene is produced with higher than thermodynamic equilibrium amount when a selectivated molecular sieve is used as catalyst for the methylation step.

SUMMARY OF THE INVENTION

This disclosure is directed to a process of manufacturing para-xylene, optionally co-manufacturing light olefins, with pygas feedstock and methylating agent.

In some embodiments, this disclosure relates to a process of manufacturing para-xylene, comprising:
(a) contacting a pygas feedstock and methylating agent with a catalyst under reaction conditions to produce a product having para-xylene, wherein the product has higher para-xylene content than the para-xylene content of the pygas feedstock; and
(b) separating the para-xylene from the product of the step (a),
wherein the catalyst comprises a molecular sieve having a Diffusion Parameter for 2,2-dimethylbutane of about 0.1-15 sec$^{-1}$ when measured at a temperature of 120° C. and a 2,2-dimethylbutane pressure of 8 kPa-a and the pygas comprises from about 1 to about 65 wt % benzene and from about 5 to 35 wt % toluene.

In some aspects of this disclosure, the catalyst is produced by a method comprising steps of:
(1) providing a porous crystalline material having a Diffusion Parameter for 2,2-dimethylbutane in excess of 15 sec$^{-1}$ when measured at a temperature of 120° C. and a 2,2-dimethylbutane pressure of 8 kPa-a; and
(2) contacting the material of step (1) with steam at a temperature in excess of 950° C. to reduce the Diffusion Parameter thereof for 2,2-dimethylbutane to about 0.1-15 sec$^{-1}$ when measured at a temperature of 120° C. and a 2,2-dimethylbutane pressure of 8 kPa-a, the micropore volume of the steamed material being at least 50 vol. % of the unsteamed material.

In other embodiments, this disclosure relates to a process of co-manufacturing light olefins and para-xylene, comprising:
(a) contacting a pygas feedstock and methylating agent with a catalyst under reaction conditions to produce a product having the light olefins and para-xylene, wherein the product has higher para-xylene content than the para-xylene content of the pygas feedstock; and
(b) separating the para-xylene from the product of the step (a),
wherein the catalyst comprises a molecular sieve having a Diffusion Parameter for 2,2-dimethylbutane of about 0.1-15 sec$^{-1}$ when measured at a temperature of 120° C. and a 2,2-dimethylbutane pressure of 8 kPa-a and the pygas comprises at least 1 wt % non-aromatic components, from about 15 to about 65 wt % benzene, and from about 5 to 35 wt % toluene, wherein the light olefins comprise ethylene and propylene, and
wherein the catalyst is produced by a method comprising steps of:
(1) providing a porous crystalline material having a Diffusion Parameter for 2,2-dimethylbutane in excess of 15 sec$^{-1}$ when measured at a temperature of 120° C. and a 2,2-dimethylbutane pressure of 8 kPa-a; and
(2) contacting the material of step (1) with steam at a temperature in excess of 950° C. to reduce the Diffusion Parameter thereof for 2,2-dimethylbutane to about 0.1-15 sec$^{-1}$ when measured at a temperature of 120° C. and a 2,2-dimethylbutane pressure of 8 kPa-a, the micropore volume of the steamed material being at least 50 vol. % of the unsteamed material.

In the embodiments of co-manufacturing light olefins and para-xylene, at least a portion of the light olefins is made by a process comprising the following reactions:
(b1) reacting methylating agent to form light olefins;
(b2) de-ethylating of ethylbenzene or polymethylated ethylbenzene; and/or
(b3) cracking of non-aromatic compounds in the pygas feedstock.

In some aspects of this disclosure, at least a portion of the para-xylene is made by a process comprising the following reactions:
(a1) methylating at least a portion of the ethylbenzene to form polymethylated ethylbenzene(s);
(a2) de-ethylating at least a portion of polymethylated ethylbenzene(s) to form para-xylene; and
(a3) methylating toluene to form para-xylene.

In some aspects of this disclosure, the pygas feedstock further comprises from about 1 to 15 wt % $C_8$ aromatic compounds and at least 20% of the $C_8$ aromatic compounds is ethylbenzene.

In yet other embodiments, this disclosure relates to a light olefins and para-xylene co-manufacturing system comprising:
(a) a steam cracking unit adapted for steam cracking a hydrocarbon feedstock to light olefins and pygas;
(b) a first separating unit adapted for separating the light olefins from the pygas;
(c) a methylation unit adapted to methylating at least a portion of the pygas from (b) to produce a product containing para-xylene; and
(d) a second separating unit adapted for separating the para-xylene from the product of step (c).

The light olefins and para-xylene co-manufacturing system may further comprise a hydroprocessing unit adapted for hydroprocessing crude and/or resid feedstock to form naphtha suitable as a feedstock for the steam cracking unit.

The light olefins and para-xylene co-manufacturing system may further comprise a transalkylation unit adapted to translate $C_9$+ aromatics to xylenes.

In other embodiments, this disclosure relates to a process of co-manufacturing light olefins and para-xylene, comprising:
(a) steam cracking a feedstock comprising at least one of vacuum gas oil, atmospheric gas oil, light naphtha, full range naphtha, ethane, propane, butane, naphtha made by a process using resid feed, or any combination thereof to form a product comprising pygas and light olefins;
(b) separating said light olefins from said pygas;
(c) contacting said pygas and a methylating agent with a catalyst under reaction conditions to produce a product having para-xylene, wherein said product has higher para-xylene content than the para-xylene content of the pygas feedstock; and
(b) separating said para-xylene from the product of the step (c),
wherein said catalyst comprises a molecular sieve having a Diffusion Parameter for 2,2-dimethylbutane of about 0.1-15 sec$^{-1}$ when measured at a temperature of 120° C. and a 2,2-dimethylbutane pressure of 8 kPa-a and said pygas comprises at least 1 wt % non-aromatic components, from about 15 to about 65 wt % benzene, and from about 5 to 35 wt % toluene, wherein said light olefins comprise ethylene and propylene, and
wherein said catalyst is produced by a method comprising steps of:
(1) providing a porous crystalline material having a Diffusion Parameter for 2,2-dimethylbutane in excess of 15 sec$^{-1}$ when measured at a temperature of 120° C. and a 2,2-dimethylbutane pressure of 8 kPa-a; and
(2) contacting the material of step (1) with steam at a temperature in excess of 1000° C. to reduce the Diffusion Parameter thereof for 2,2-dimethylbutane to about 0.1-15 sec$^{-1}$ when measured at a temperature of 120° C. and a 2,2-dimethylbutane pressure of 8 kPa-a, the micropore volume of the steamed material being at least 50% of the unsteamed material.

In some aspects, the pygas separated in step (b) supplies to the methylation step without any processing. In other aspects, the pygas separated in step (b) is subjected to a de-benzene process to remove at least a portion of the benzene in the pygas prior to the contacting step. In yet other aspects, the pygas separated in step (b) is subjected to a hydrotreating process to remove at least a portion of the multi-olefins in the pygas prior to the contacting step. In yet other aspects, the pygas separated in step (b) is subjected to a hydrotreating process to remove at least a portion of the multi-olefins and at least a portion of mono-olefins in the pygas prior to the contacting step. In yet other aspects, the pygas separated in step (b) is subjected to any combination of a de-benzene process, a hydrotreating process to remove at least a portion of the multi-olefins, at least a portion of the mono-olefins, and/or optionally without an extraction process to remove at least a portion of the benzene and/or at least a portion of the paraffins, in the pygas prior to the contacting step.

These and other objects, features, and advantages will become apparent as reference is made to the following detailed description, preferred embodiments, examples, and appended claims.

DETAILED DESCRIPTION

Figure 1:
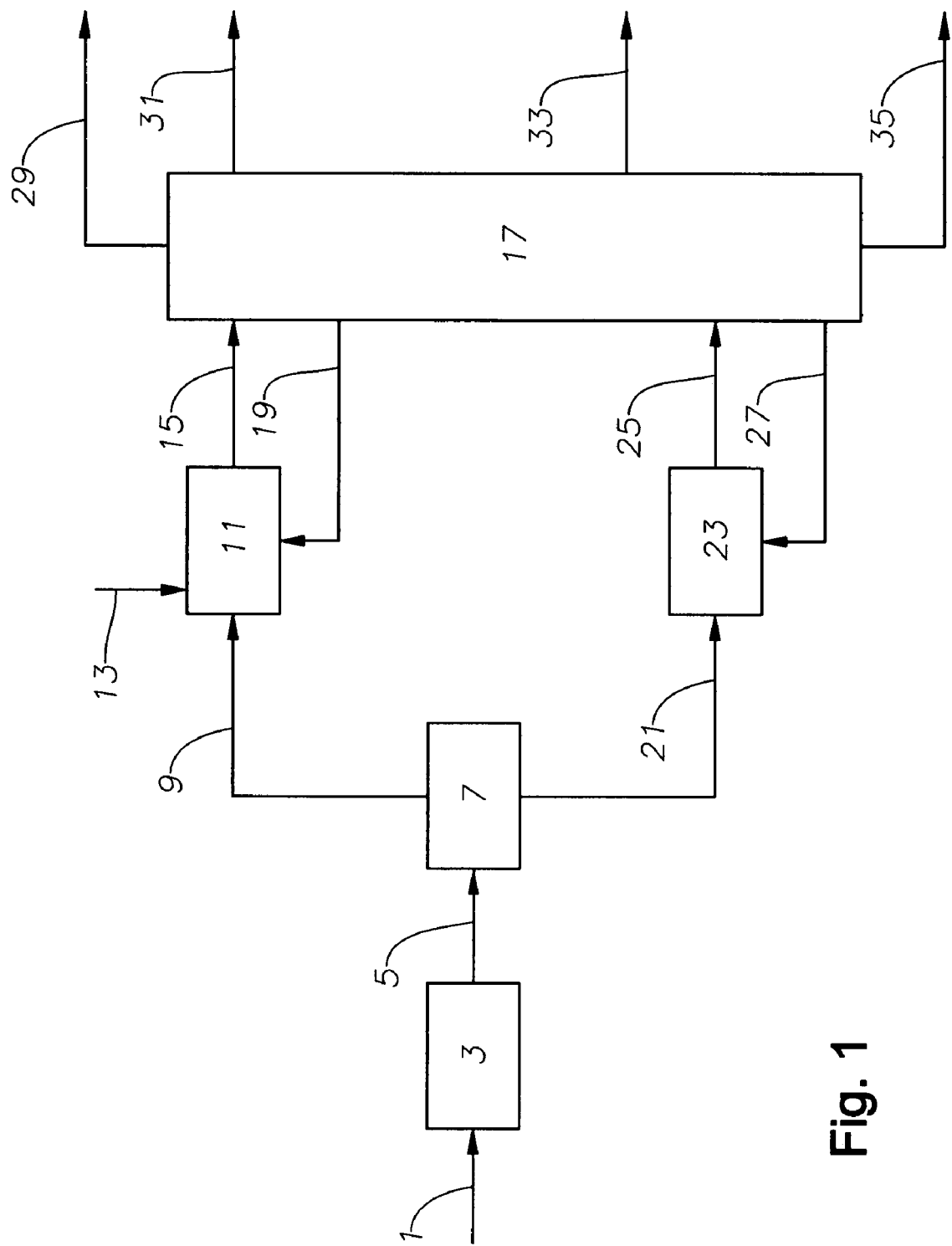
FIG. 1 is a process flow diagram illustrating one embodiments of the disclosure simulated in Example 1.

This disclosure provides a means to produce para-xylene from pygas. In a preferred embodiment, para-xylene is produced from pygas without extraction. In some embodiments, pygas and methylating agent are converted in high selectivity to ethylene, propylene and para-xylene. In some embodiments, the pygas useful for this disclosure is produced by cracking hydrotreated polycyclic napthenes and aromatics, which is rich in benzene, toluene and $C_8$ aromatics. In other embodiments, pygas useful for this disclosure is subjected to a benzene removal process prior to the methylation step. The process of this disclosure provides a novel means of producing para-xylene using pygas and methylating agent, especially pygas made from steam cracking of naphtha from crude and/or resid. In a preferred embodiment, this disclosure relates to a method of selectively producing para-xylene from pygas.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "wppm" as used herein is defined as parts per million by weight.

All weights of molecular sieve, weights of binder, and weights of catalyst composition, as used in herein, are calculated or measured based on the calcined weight basis (i.e., calcined at 510° C. in air for at least one hour).

The term "hydroprocessing" as used herein includes hydrofining and hydrocracking.

The term "steam cracker" as used herein is also known more generally as a thermal pyrolysis unit; both terms are well-known in the art. Steam, although optional, is typically added among other reactants to reduce hydrocarbon partial pressure, to control residence time, and to minimize coke formation. In preferred embodiments the steam may be superheated, such as in the convection section of the pyrolysis unit, and/or the steam may be sour or treated process steam.

Crude, as used herein, means whole crude oil as it issues from a wellhead, optionally including a step of desalting and/or other steps as may be necessary to render it acceptable for conventional distillation in a refinery. Crude as used herein is presumed to contain resid.

Resid as used herein refers to the complex mixture of heavy petroleum compounds otherwise known in the art as residuum or residual. Atmospheric resid is the bottoms product produced in atmospheric distillation when the endpoint of the heaviest distilled product is nominally 650° F. (343° C.), and is referred to as 650° F.+ resid. Vacuum resid is the bottoms product from a column under vacuum when the heaviest distilled product is nominally 1050° F. (566° C.), and is referred to as 1050° F.+ resid. (The term "nominally" means here that reasonable experts may disagree on the exact cut point for these terms, but probably by no more than ±50° F. or at most ±100° F.). This 1050° F.+ portion contains asphaltenes, which traditionally are considered to be an anathema to the steam cracker, resulting in corrosion and fouling of the apparatus. The term "resid" herein means 650° F,+ (343° C.+) resid and 1050° F.+ (566° C.+) resid unless otherwise specified; note that 650° F.+ (343° C.+) resid comprises 1050° F.+ (566° C.+) resid.

The term "$C_n$" hydrocarbon wherein n is a positive integer, e.g., 1, 2, 3, 4, 5, 6, 7, 8, 9, 10, 11, 12, as used herein, means a hydrocarbon having n number of carbon atom(s) per molecule. For example, a $C_n$ aromatic compound means an aromatic compound having n number of carbon atom(s) per molecule; likewise $C_n$ paraffin compound and $C_n$ olefin compound. The term "$C_n+$" hydrocarbon wherein n is a positive integer, e.g., 1, 2, 3, 4, 5, 6, 7, 8, 9, 10, 11, 12, as used herein, means a hydrocarbon having at least n number of carbon atom(s) per molecule. The term "$C_n-$" hydrocarbon wherein n is a positive integer, e.g., 1, 2, 3, 4, 5, 6, 7, 8, 9, 10, 11, 12, as used herein, means a hydrocarbon having no more than n number of carbon atom(s) per molecule.

The term "$C_n$ feedstock", wherein n is a positive integer, e.g., 1, 2, 3, 4, 5, 6, 7, 8, 9, 10, 11, 12, as used herein, means that greater than 50 wt % of the $C_n$ feedstock comprises hydrocarbons having n number of carbon atom(s) per molecule. The term "$C_n+$ feedstock", wherein n is a positive integer, e.g., 1, 2, 3, 4, 5, 6, 7, 8, 9, 10, 11, 12, as used herein, means that greater than 50 wt % of the $C_n+$feedstock comprises hydrocarbons having at least n number of carbon atom(s) per molecule. The term "$C_n-$ feedstock" wherein n is a positive integer, e.g., 1, 2, 3, 4, 5, 6, 7, 8, 9, 10, 11, 12, as used herein, means that greater than 50 wt % of the $C_n-$feedstock comprises hydrocarbons having no more than n number of carbon atom(s) per molecule. The term "$C_n$ aromatics", wherein n is a positive integer, e.g., 1, 2, 3, 4, 5, 6, 7, 8, 9, 10, 11, 12, as used herein, means that greater than 50 wt % of the $C_n$ aromatics comprises aromatics having n number of carbon atom(s) per molecule. The term "$C_n+$ aromatics", wherein n is a positive integer, e.g., 1, 2, 3, 4, 5, 6, 7, 8, 9, 10, 11, 12, as used herein, means that greater than 50 wt % of the $C_n+$ aromatics comprises aromatics having at least n number of carbon atom(s) per molecule. The term "$C_n-$ aromatics" wherein n is a positive integer, e.g., 1, 2, 3, 4, 5, 6, 7, 8, 9, 10, 11, 12, as used herein, means that greater than 50 wt % of the $C_n$- aromatics comprises aromatics having no more than n number of carbon atom(s) per molecule.

The term "shape-selective catalysis" describes catalytic selectivities in zeolites. The principles behind shape selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of a feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective toluene disproportionation to para-xylene.

Pygas Feedstock

Thermal cracking of hydrocarbons is a petrochemical process that is widely used to produce light olefins, e.g., ethylene, propylene and butylenes, and aromatics, e.g., benzene, toluene and xylenes. Typically feedstocks for thermal cracking process are naphtha, gas oil or other fractions of whole crude oil. The steam/hydrocarbon mixture is preheated in the radiant section of a pyrolysis unit prior to entering the convection section, where it is very quickly heated, such as at pressures ranging from about 100 kPa-a (kilopascal absolute) to about 350 kPa-a, to a severe hydrocarbon cracking temperature in the range from about 600° C. to about 900° C.

After cracking, the effluent from the pyrolysis furnace contains gaseous hydrocarbons of great variety, e.g., saturated, monounsaturated, and polyunsaturated, and can be aliphatic and/or aromatic, as well as significant amounts of hydrogen. The cracked product is then further processed in the olefin production plant to produce the various separate individual streams of, i.e., hydrogen, the light olefins ethylene, propylene, butenes, and aromatic compounds, as well as other products such as pygas.

The starting feedstock for a conventional olefin production plant has been subjected to processing before it reaches the plant. Normally, whole crude is first subjected to desalting prior to being distilled or otherwise fractionated into a plurality of parts (fractions) such as gasoline, kerosene, naphtha, gas oil (vacuum or atmospheric) and the like, including a high boiling residuum ("resid"). Thereafter, conventionally, any of these fractions, other than the resid, are passed to an olefin production plant as the feedstock for that plant.

The pygas is a byproduct of olefins production by steam cracking hydrocarbons such as naphtha of gas oil feedstocks. The pygas contains a high proportion of aromatics, primarily benzene and toluene, and a smaller amount of $C_8$ aromatics that contains up to 40 percent by weight of ethylbenzene. Pygas yields and compositions are determined by the severity of the cracking operation and the composition of feedstocks to the cracking process. Normally, a pygas comprises 15 to 65 wt % benzene, alternatively 20-60 wt % benzene, or 30-50 wt % benzene; 5-35 wt % toluene, alternatively 10-25 wt % toluene, or 15-25 wt % toluene; 1-15 wt % $C_8$ aromatic compounds, alternatively 3-10 wt % $C_8$ aromatic compounds, or 4-9 wt % $C_8$ aromatic compounds; 0.1-6 wt % ethylbenzene, alternatively 0.5-3 wt % ethylbenzene, or 1-1.5 wt % ethylbenzene; 1-15 wt % non-aromatics, alternatively 2-10 wt % non-aromatics, or 5-10 wt % non-aromatics, and about 0.1 to 5 wt % unsaturated non-aromatics, alternatively 0.1 to 2 wt % unsaturated non-aromatics, or 0.2 to 1 wt % unsaturated non-aromatics; optionally 0.001 to 2 wt % multi-unsaturated non-aromatics, such as di-olefins. Prior to recovering benzene and toluene, a pygas is normally subjected to hydrotreating process to remove olefinic components and extraction process to remove non-aromatics. The pygas after extraction normally comprises less than 1 wt % non-aromatics, preferably less than 0.5 wt % non-aromatics. The benzene and toluene may be separated by conventional method of separation such as distillation.

In some embodiments of this disclosure, the pygas useful for this disclosure has a benzene concentration ranging from about 15 wt % to about 65 wt %. In other embodiments of this disclosure, the pygas useful for this disclosure has been subjected to a benzene removal step wherein the benzene concentration is less than 15 wt %, e.g., from about 1 wt % to about 14 wt %. The following benzene concentrations are useful lower benzene concentration limits for all disclosure processes: 1, 2, 5, 10, 15, 20, 25, 30, 35, 40, 45, 50, 55 and 60 wt %. The following benzene concentrations are useful upper benzene concentration limits for all disclosure processes: 5, 10, 15, 20, 25, 30, 35, 40, 45, 50, 55, 60 and 65 wt %. The benzene concentration falls in a range between any one of the above-mentioned lower limits and any one of the above-mentioned upper limits, so long as the lower limit is less than or equal to the upper limit. The benzene concentration may be present in an amount ranging from 15 wt % to 65 wt % in one embodiment, alternatively 1 wt % to 5 wt %, alternatively from 30 wt % to 50 wt %, and alternatively 35 wt % to 40 wt % in another embodiment.

In some embodiments of this disclosure, the pygas useful for this disclosure has a toluene concentration ranging from about 5 wt % to about 35 wt %. The following toluene concentrations are useful lower toluene concentration limits for all disclosure processes: 5, 10, 15, 20, 25 and 30 wt %. The following toluene concentrations are useful upper toluene concentration limits for all disclosure processes: 10, 15, 20, 25, 30 and 35 wt %. The toluene concentration falls in a range between any one of the above-mentioned lower limits and any one of the above-mentioned upper limits, so long as the lower limit is less than or equal to the upper limit. The toluene concentration may be present in an amount ranging from 5 wt % to 35 wt % in one embodiment, alternatively 10 wt % to 30 wt %, alternatively from 15 wt % to 25 wt %, and alternatively 15 wt % to 20 wt % in another embodiment.

In some embodiments of this disclosure, the pygas useful for this disclosure has a $C_8$ aromatic concentration ranging from about 1 wt % to about 15 wt %. The following $C_8$ aromatic concentrations are useful lower $C_8$ aromatic concentration limits for all disclosure processes: 1, 2, 3, 4, 5, 6, 7, 8, 9, 10, 11, 12, 13 and 14 wt %. The following $C_8$ aromatic compounds concentrations are useful upper $C_8$ aromatic concentration limits for all disclosure processes: 2, 3, 4, 5, 6, 7, 8, 9, 10, 11, 12, 13, 14 and 15 wt %. The $C_8$ aromatic concentration falls in a range between any one of the above-mentioned lower limits and any one of the above-mentioned upper limits, so long as the lower limit is less than or equal to the upper limit. The $C_8$ aromatic concentration may be present in an amount ranging from 1 wt % to 15 wt % in one embodiment, alternatively 3 wt % to 10 wt %, alternatively from 4 wt % to 9 wt %, and alternatively 5 wt % to 8 wt % in another embodiment.

In some embodiments of this disclosure, the pygas useful for this disclosure has an ethylbenzene concentration ranging from about 0.1 wt % to about 6 wt %. The following ethylbenzene concentrations are useful lower ethylbenzene concentration limits for all disclosure processes: 0.1, 0.2, 0.5, 1, 1.5, 2, 2.5, 3, 3.5, 4, 4.5, 5 and 5.5 wt %. The following ethylbenzene concentrations are useful upper ethylbenzene concentration limits for all disclosure processes: 0.2, 0.5, 1, 1.5, 2, 2.5, 3, 3.5, 4, 4.5, 5, 5.5 and 6 wt %. The ethylbenzene concentration falls in a range between any one of the above-mentioned lower limits and any one of the above-mentioned upper limits, so long as the lower limit is less than or equal to the upper limit. The ethylbenzene concentration may be present in an amount ranging from 0.1 wt % to 6 wt % in one embodiment, alternatively 0.5 wt % to 3 wt %, alternatively from 1 wt % to 1.5 wt %, and alternatively 0.1 wt % to 2 wt % in another embodiment.

In some embodiments of this disclosure, the pygas useful for this disclosure has a non-aromatics concentration ranging from about 1 wt % to about 15 wt %. The following non-aromatics concentrations are useful lower non-aromatics concentration limits for all disclosure processes: 1, 2, 3, 4, 5, 6, 7, 8, 9, 10, 11, 12, 13 and 14 wt %. The following non-aromatics concentrations are useful hupper non-aromatics concentration limits for all disclosure processes: 2, 3, 4, 5, 6, 7, 8, 9, 10, 11, 12, 13, 14 and 15 wt %. The non-aromatics concentration falls in a range between any one of the above-mentioned lower limits and any one of the above-mentioned upper limits, so long as the lower limit is less than or equal to the upper limit. The non-aromatics concentration may be present in an amount ranging from 1 wt % to 15 wt % in one embodiment, alternatively 3 wt % to 10 wt %, alternatively from 4 wt % to 9 wt %, and alternatively 5 wt % to 8 wt % in another embodiment.

In some embodiments of this disclosure, the pygas useful for this disclosure has an unsaturated non-aromatics concentration ranging from about 0.1 wt % to about 5 wt %. The following unsaturated non-aromatics concentrations are useful lower unsaturated non-aromatics concentration limits for all disclosure processes: 0.1, 0.2, 0.5, 1, 1.5, 2, 2.5, 3, 3.5, 4, and 4.5 wt %. The following unsaturated non-aromatics concentrations are useful upper unsaturated non-aromatics concentration limits for all disclosure processes: 0.2, 0.5, 1, 1.5, 2, 2.5, 3, 3.5, 4, 4.5 and 5 wt %. The unsaturated non-aromatics concentration falls in a range between any one of the above-mentioned lower limits and any one of the above-mentioned upper limits, so long as the lower limit is less than or equal to the upper limit. The unsaturated non-aromatics concentration may be present in an amount ranging from 0.1 wt % to 5 wt % in one embodiment, alternatively 0.1 wt % to 2 wt %, alternatively from 0.2 wt % to 1 wt %, and alternatively 0.1 wt % to 1 wt % in another embodiment.

Optionally, the pygas useful for this disclosure has a multi-unsaturated non-aromatics concentration ranging from about 0.001 wt % to about 2 wt %. The following multi-unsaturated non-aromatics concentrations are useful lower multi-unsaturated non-aromatics concentration limits for all disclosure processes: 0.001, 0.005, 0.01, 0.05, 0.1, 0.5, 1 and 1.5 wt %. The following multi-unsaturated non-aromatics concentrations are useful upper multi-unsaturated non-aromatics concentration limits for all disclosure processes: 0.005, 0.01, 0.05, 0.1, 0.5, 1, 1.5 and 2 wt %. The multi-unsaturated non-aromatics concentration falls in a range between any one of the above-mentioned lower limits and any one of the above-mentioned upper limits, so long as the lower limit is less than or equal to the upper limit. The multi-unsaturated non-aromatics concentration may be present in an amount ranging from 0.001 wt % to 2 wt % in one embodiment, alternatively 0.01 wt % to 1 wt %, alternatively from 0.1 wt % to 2 wt %, and alternatively 0.5 wt % to 1 wt % in another embodiment.

Pygas made from Resid feedstock

It has previously been proposed to upgrade certain crude fractions, prior to steam cracking, by first hydroprocessing the feed. For instance, U.S. Pat. Nos. 3,855,113 and 6,190,533 are directed to an integrated process comprising passing the feed to a hydrotreating zone followed by a steam cracking zone. In neither case, however, is whole crude or a fraction comprising resid passed directly to the hydrotreating zone. See also GB 2071133 and Erdoel & Kohle, Erdgas, Petrochemie (1981), 34(1), 443-6.

Other references of interest include U.S. Pat. Nos. 3,855,113; 4,057,490; 4,179,355; and 6,743,961.

Resid hydroprocessing is a known process for upgrading resid to fuels such as fuel oil, diesel, heating oil, jet, kerosene, gasoline, LPG, and fuel gas. Each of these is useful per se as fuels and/or as intermediates for the production of, for instance, petrochemicals. By way of example, fuel oil may be cracked to produce the lighter boiling fuels gasoline, LPG, and fuel gas and/or the petrochemicals ethylene, propylene, and butanes.

Typically resid hydroprocessing is carried out at a temperature from about 260 to 482° C., preferably 343 to 482° C. A pressure from about 3500 to 69000 kPa-a, preferably 5500 to 27300 kPa-a, is used, with a liquid hourly space velocity from 0.1 to 5 $hr^{-1}$, preferably 0.25 to 1 $hr^{-1}$. The hydrogen supply rate (makeup and recycle hydrogen) to the hydroconversion zone is in the range from about 14.16 to about 566 standard cubic meter per 158.9 liters (barrel) of hydrocarbon feed, preferably about 56.6 to 142 standard cubic meter per 158.9 liters (barrel). The hydroprocessing may be carried out utilizing two or more hydroprocessing zones. For example, in one embodiment a first zone with a first catalyst can be designed to accumulate most of the metals removed from the feedstock, a second zone with a second catalyst can be designed for maximum heteroatom removal and aromatics hydrogenation. In another embodiment, a first catalyst can be designed to accumulate most of the metals removed from the feedstock, a second zone with a second catalyst can be designed for maximum heteroatom removal and a third zone with a third catalyst can be designed to increase aromatics hydrogenation.

The catalyst employed in the typical commercial hydroconversion zone(s) is comprised of material having hydrogenation-dehydrogenation activity together with an amorphous carrier. Exemplary amorphous carriers include alumina, silica-alumina, silica, zirconia, or titania. Hydrogenation-dehydrogenation components of the catalyst preferably comprise at least one hydrogenation component selected from Group 6 metals and compounds of Group 6 metals and at least one hydrogenation component selected from Groups 8-10 metals and compounds of Groups 8-10 metals. Preferred combinations of hydrogenation components include nickel sulfide with molybdenum sulfide, cobalt sulfide with molybdenum sulfide, cobalt with molybdenum, and nickel with tungsten. The catalyst employed in the disclosure may also be comprised of a material having hydrogenation-dehydrogenation activity formulated without an amorphous carrier. Exemplary catalysts include Nebula.

In a preferred embodiment, the effluent selected to be steam cracked comprises a fraction boiling from about 371 to about 482° C. In another preferred embodiment, the hydroprocessor effluent, if it contains any resid, is first treated to remove the resid prior to feeding the material into the convection section of the thermal pyrolysis unit (or steam cracker).

In another embodiment of the disclosure, a resid-containing crude or fraction thereof is treated by a process including a first step of hydroprocessing and a second step of thermal cracking.

Crude fractions are typically obtained from the refinery pipestill. Although any crude fraction obtained from the refinery pipestill is useful in the present disclosure, the significant advantage offered by the present disclosure is that crude fractions still containing all or a portion of the original resid present in the whole crude obtained from the wellhead may be processed.

In a preferred embodiment, wherein the feed comprises crude or atmospheric resids that contain appreciable amounts of 1050° F.+ (566° C.+) resides, e.g., 10 wt % or more of resid, or 20 wt % or more of resid, the resid-containing feed, after hydroprocessing, is passed into the convection section of a pyrolysis unit, where it is preheated. Then it is passed to a flash drum, which may be optionally integrated with the pyrolysis unit, to drop out the heaviest fraction (e.g., substantially all the asphaltenes). The terms "flash drum", "flash pot", "knock-out drum" and "knock-out pot" are used interchangeably herein; they are per se well-known in the art. In a preferred embodiment, the composition of the vapor phase leaving the flash drum is substantially the same as the composition of the vapor phase entering the flash drum, and likewise the composition of the liquid phase leaving the flash drum is substantially the same as the composition of the liquid phase entering the flash drum, i.e., the separation in the flash drum consists essentially of a physical separation of the two phases entering the drum. In a more preferred embodiment the material is treated by visbreaking or mild thermal cracking to increase the proportion of vapor phase at the expense of bottoms product. Visbreaking and mild thermal cracking are per se well-known in the art.

The preferred flash drums and their integration with pyrolysis units have previously been described in U.S. Patent Application Publication Nos. 2004/0004022, 20040004027, and 2004/0004028, and more recently in U.S. application Ser. No. 11/068,615 filed Feb. 28, 2005, Ser. No. 10/851,486 filed May 21, 2004, Ser. No. 10/851,546 filed on May 21, 2004, Ser. No. 10/851,878 filed May 21, 2004, Ser. No. 10/851,494 filed on May 21, 2004, Ser. No. 10/851,487 filed May 21, 2004, Ser. No. 10/851,434 filed May 21, 2004, Ser. No. 10/851,495 filed May 21, 2004, Ser. No. 10/851,730 filed May 21, 2004, Ser. No. 10/851,500 filed May 21, 2004, Ser. No. 11/134,148 filed May 20, 2005, Ser. No. 10/975,703 filed Oct. 28, 2004, Ser. No. 10/891,795 filed Jul. 14, 2004, Ser. No. 10/891,981 filed Jul. 14, 2004, Ser. No. 10/893,716 filed Jul. 16, 2004, Ser. No. 11/009,661 filed Dec. 10, 2004, Ser. No. 11/177,076 filed Jul. 8, 2005; and Ser. No. 11/231,490, filed Sep. 20, 2005. Another preferred apparatus effective as a flash pot for purposes of the present disclosure is described in U.S. Pat. No. 6,632,351 as a "vapor/liquid separator".

In the process of the present disclosure, the flash drum preferably operates at a temperature of between about 425° C. and about 455° C. Passing material through the flash drum to obtain an overhead vapor and liquid bottoms is referred to herein as "flashing".

Crude or resid-containing fraction thereof, particularly atmospheric resid, vacuum resid, or any asphaltene-containing refinery or chemical intermediate stream is also a preferred feed. When the feed comprises greater than about 0.1 wt %, or preferably greater than about 5.0 wt % asphaltenes, a flash pot is advantageously used to remove the asphaltenes prior to entering the radiant section of the pyrolysis unit. The flash drum may be integrated with the pyrolysis unit, as discussed above, so that the feed is preheated in the convection section of the pyrolysis unit prior to entering the flash pot. In the alternative, it may be a separate unit so that removal of asphaltene occurs substantially prior to entering the pyrolysis unit.

Other preferred feeds include a hydrocarbon stream having a high concentration of polycyclic aromatics, particularly those high in heterocyclic rings, tar, and topped crude ("topped crude" being the cut roughly from about 260-315° C. and higher cut, but below temperatures where significant cracking occurs, e.g., about 340-370° C.; often topped crude is used as a synonym for atmospheric resid). This preferred feed may or may not contain appreciable amounts of resid.

Upgrading of crude and crude fractions containing resid and also an appreciable amount of polycyclic aromatics, particularly those high in heterocyclic rings, is one of the particular advantages provided by the present disclosure. An example is VGO (Vacuum Gas Oil) upgrading. Hydrotreating alone provides for some breaking of the ring structures of the aromatic heterocycles, however, a very large portion of the polycyclic ring structure is left intact. Steam cracking alone provides for a product comprising significant yields of fuel oil, tar, and non-aromatics in addition to the desired ethylene, propylene, butanes, $C_5$ olefins and dienes, and single-ring aromatic products. However, in a process according to the present disclosure, hydrotreating followed by steam cracking simultaneously reduces the yields of fuel oil, tar, and non-aromatics while increasing the yield of the aforementioned desirable petrochemical products. In addition to resid, resid-derived VGO, feeds comprising crudes, light catalytic cycle oil (LCCO or distillate from a catalytic cracker), coker gas-oils, FCC cycle oils, steam cracker tar and lube extracts are preferred feeds to arrive at a product rich in the aforementioned preferred aromatics.

Thus, hydroprocessing feedstocks rich in polynuclear aromatics, particularly those high in heterocyclic rings, are a preferred feedstock for producing light olefins and single-ring aromatics in a steamcracker. Polynuclear aromatics comprise both aromatic and naphthenic ring structures. Without wishing to be bound by theory, such feedstocks, when fed to a steamcracker, undergo hydrogen transfer reactions, whereby naphthenic rings are converted to aromatic rings. The hydrogen atoms removed from the naphthenes typically emerge from the steamcracker as C—H bonds in light paraffin molecules such as methane, ethane, and propane. In mole%, methane is the dominant paraffin produced in steamcracking. Thus, feedstocks rich in polynuclear aromatics, particularly those high in heterocyclic rings, tend to produce high yields of methane and tar upon steamcracking. The present inventors have surprisingly discovered that high severity hydroprocessing of these feedstreams results in the production of a high quality steamcracker feedstock.

In a preferred embodiment, increasing the severity of the steam cracker using at least one of the aforementioned feeds increases the yield of benzene toluene and xylenes. Reaction Severity is a term known per se in the art and can be measured, for instance, by the ratio of propylene versus methane exiting the steam cracker.

The pygas obtained from steam cracking a hydrocarbon feedstock made with hydroprocessed resid contains at least 1 wt % (based on the total weight of the pygas), alternatively 2 wt %, 3 wt % more aromatics than the pygas obtained from conventional hydrocarbon feedstocks, e.g., light naphtha, $C_2$, $C_3$, AGO, VGO, and LCCO. The pygas obtained from steam cracking a hydroprocessed feedstock made with hydroprocessed resid or combined with the pygas obtained from conventional hydrocarbon feedstocks, e.g., light naphtha, $C_2$, $C_3$, AGO, VGO, and LCCO is a preferred feedstock for the methylation process of this disclosure.

While the above embodiments have been illustrated using, as feed, atmospheric resid, the feed advantageously may be also be selected from heavy crude oil, atmospheric and vacuum resids, fuel oil, FCC cycle oils, coker gasoils, cracker tar, topped crude, and any other feed containing resid and/or a high concentration of multicyclic heteroatom aromatic species. Mixtures of such feeds, such as provided by crude, are also preferred.

In some preferred embodiments, the feed to the steam cracking process comprises at least one of vacuum gas oil, atmospheric gas oil, light naphtha, full range naphtha, ethane, propane, butane, naphtha made by a process using resid feed, or any combination thereof.

Methylation Process

The production of PX is typically performed by toluene disproportionation over a catalyst under conversion conditions. Examples include the toluene disproportionation, as described by Pines in "The Chemistry of Catalytic Hydrocarbon Conversions", Academic Press, N.Y., 1981, p. 72. Such methods typically result in the production of a mixture including PX, OX, and MX. Depending upon the degree of selectivity of the catalyst for PX (para-selectivity) and the reaction conditions, different percentages of PX are obtained. The yield, i.e., the amount of xylene produced as a proportion of the feedstock, is also affected by the catalyst and the reaction conditions.

The equilibrium reaction for the conversion of toluene to xylene and benzene products normally yields about 24 wt % PX, about 54 wt % MX, and about 22 wt % OX among xylenes.

U.S. Pat. No. 6,423,879 discloses a process for the selective production of para-xylene which comprises reacting toluene with methanol in the presence of a catalyst comprising a porous crystalline material having a Diffusion Parameter for 2,2 dimethylbutane of about 0.1-15 $\sec^{-1}$ when measured at a temperature of 120° C. and a 2,2 dimethylbutane pressure of 8 kPa-a. The porous crystalline material is preferably a medium-pore zeolite, particularly ZSM-5, which has been severely steamed at a temperature of at least 950° C. The porous crystalline material is preferably combined with at least one oxide modifier, preferably including phosphorus, to control reduction of the micropore volume of the material during the steaming step.

In a preferred embodiment, a pygas feedstock, e.g., pygas made steam cracking of naphtha, is supplied to a methylation reaction zone together with methylating agent, e.g., methanol, the mixture of pygas and methylating agent is contacted with a catalyst to produce a product having para-xylene, $C_5$-, benzene, toluene, and $C_9$+. The pygas useful for the process of this disclosure comprises at least one of steam cracking vacuum gas oil pygas, steam cracking atmospheric gas oil pygas, steam cracking light naphtha pygas, steam cracking full range naphtha pygas, steam cracking ethane pygas, steam cracking propane pygas, steam cracking butane pygas, and steam cracking naphtha made by a process using resid feed pygas. The product is further subjected to a separation step to separate at least a portion of $C_5$-, benzene, toluene, or benzene/toluene, $C_9$+, and para-xylene. In one embodiment, at least a portion of the benzene, toluene, or benzene/toluene separated is recycled to the methylation reaction zone. In another embodiment, the $C_9$+ separated from the methylating product is sent to a transalkylation reaction zone, wherein the $C_9$+ and a benzene/toluene feedstock is in contact with a transalkylation catalyst to product more para-xylene.

The methylation reaction conditions comprises a temperature between about 500 and about 700° C., preferably between about 500 and about 600° C., a pressure of between about 100 to about 7000 kPa-a, a weight hourly space velocity of between about 0.5 and 1000 $hr^{-1}$, and a molar ratio of toluene to methylating agent (in the reactor charge) of at least about 0.2, e.g., from about 0.2 to about 20. The process is preferably conducted in the presence of added hydrogen and/or added water such that the molar ratio of hydrogen and/or water to toluene+methylating agent in the feed is between about 0.01 and about 10.

The transalkylation reaction can be conducted in any appropriate reactor including a radial flow, fixed bed, continuous down flow or fluid bed reactor. The transalkylation reaction conditions typically include a temperature ranging from about 343° C. to about 510° C., such as from about 400° C. to about 454° C.; a pressure from about 380 to about 4240 kPa-a, such as from about 1480 to about 3550 kPa-a; a hydrogen to hydrocarbon molar ratio from about 1 to about 5, such as from about 1 to about 3 and a WHSV of about 0.2 to about 20, such as from 1 to about 5. The transalkylation reaction conditions are sufficient to convert the heavy aromatic feed to a product containing substantial quantities of $C_6$-$C_8$ aromatic compounds, such as benzene, toluene and xylenes, especially benzene and xylene.

The isomerization reaction conditions are selected so as to be effective to isomerize the xylenes in the feedstock. Suitable conditions include conditions include a temperature of about 120° C. to about 260° C., a pressure of about 445 to about 7000 kPa-a and WHSV of about 0.1 to about 100 $hr^{-1}$. More preferably, the conditions include a temperature of about 160° C. to about 232° C., a pressure of about 790 to about 3550 kPa-a and WHSV of about 1 to about 30 $hr^{-1}$. In general, the processes in the second reactor are conducted in the absence of added hydrogen.

The product stream from the methylation step comprises para-xylene, $C_8$ aromatics, optionally light gas, benzene, toluene and $C_9$+. The product may subject to a step of separating at least a portion of light gas to form a light gas product, at least a portion of the benzene and toluene to form a BT product having at least # wt % benzene and at least # wt % toluene and at least a portion of the $C_9$+ to form a $C_9$+ product. In some preferred embodiments, at least a portion of the BT product separated is recycled back to the methylation step. The $C_9$+ product may be transalkylated with benzene and/or toluene to form xylenes.

The methylating agent useful for this disclosure comprises at least one of methanol, dimethyl ether, halogenated methane, e.g., chloromethane, syngas, e.g., CO and $H_2$ or $CO_2$ and $H_2$.

Preferably the catalyst useful for the methylation comprises porous crystalline materials having specific and closely defined diffusion characteristics, such as can be obtained by severe steaming of ZSM-5 containing an oxide modifier, exhibit improved selectivity for the xylene product contains at least about 30 wt %, preferably at least 50 wt %, more preferably at least 70 wt %, even more preferably at least 80 wt %, yet even more preferably at least 90 wt %, of the para-xylene selectivity defined as the para-xylene concentration in the xylene product measured at the conditions such that a toluene methylation conversion of 15% (based on toluene) per pass when pure toluene is fed.

In one aspect, this disclosure resides in a process for the selective production of para-xylene which comprises reacting benzene, toluene, ethylbenzene in pygas with a methylating agent, e.g., methanol, dimethylether, and/or chloromethane, under alkylation conditions in the presence of a catalyst comprising a porous crystalline material having a Diffusion Parameter for 2,2-dimethylbutane of about 0.1-15 sec$^{-1}$ when measured at a temperature of 120° C. and a 2,2-dimethylbutane pressure of 8 kPa-a.

Preferably, the porous crystalline material has a Diffusion Parameter of about 0.5-10 sec$^{-1}$.

Preferably, the catalyst contains at least one oxide modifier and more preferably at least one oxide modifier selected from oxides of elements of Groups 2, 3, 4, 5, 6, 13, 14 and 15 of the Periodic Table. Most preferably the oxide modifier is selected from oxides of boron, magnesium, calcium, lanthanum and most preferably phosphorus.

Preferably, the catalyst contains about 0.05 to about 20, more preferably about 0.1 to about 10 and most preferably about 0.1 to about 5, wt % of the oxide modifier based on elemental modifier.

Preferably, the catalyst has an alpha value less than 50 and preferably less than 10.

In a further aspect, this disclosure resides in a method for producing a catalyst for use in the selective production of para-xylene by reacting toluene with methylating agent, the method comprising the steps of: (a) starting with a porous crystalline material having a Diffusion Parameter for 2,2-dimethylbutane in excess of 15 sec$^{-1}$ when measured at a temperature of 120° C. and a 2,2-dimethylbutane pressure of 8 kPa-a; and (b) contacting the material of step (a) with steam at a temperature of at least about 950° C. to reduce the Diffusion Parameter thereof for 2,2-dimethylbutane to about 0.1-15 sec$^{-1}$ when measured at a temperature of 120° C. and a 2,2-dimethylbutane pressure of 8 kPa-a, the micropore volume of the steamed material being at least 50% of the unsteamed material.

Preferably, the porous crystalline material used in step (a) comprises an aluminosilicate zeolite having a silica to alumina molar ratio of at least 250.

The present invention provides a process for alkylating toluene with methylating agent to selectively produce para-xylene in high yield and with a high per-pass conversion of toluene. The process employs a catalyst which comprises a porous crystalline material having a Diffusion Parameter for 2,2-dimethylbutane of about 0.1-15 sec$^{-1}$, and preferably 0.5-10 sec$^{-1}$, when measured at a temperature of 120° C. and a 2,2-dimethylbutane pressure of 8 kPa-a.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_{2\infty}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The catalyst useful for the methylation comprises a porous crystalline material having a Constraint Index of 1-12, such as ZSM-5, ZSM-11 ZSM-22, ZSM-23, ZSM-48, and ITQ-13. The porous crystalline material employed in the process of this disclosure is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and para-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the process of this disclosure.

Particular examples of suitable medium pore zeolites include ZSM-5, ZSM-11, ZSM-12, ZSM-22, ZSM-23, ZSM-35, ZSM48, and MCM-22, with ZSM-5, ITQ-13 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. No. 5,304,698 to Husain; U.S. Pat. No. 5,250,277 to Kresge et al.; U.S. Pat. No. 5,095,167 to Christensen; and U.S. Pat. No. 5,043,503 to Del Rossi et al., the disclosure of which patents are incorporated by reference.

The synthetic porous crystalline material ITQ-13 is described in U.S. Pat. No. 6,471,941, which is hereby incorporated by reference. ITQ-13 is a single crystalline phase that has a unique 3-dimensional channel system comprising three sets of channels. In particular, ITQ-13 comprises a first set of generally parallel channels each of which is defined by a 10-membered ring of tetrahedrally coordinated atoms, a second set of generally parallel channels which are also defined by 10-membered rings of tetrahedrally coordinated atoms and which are perpendicular to and intersect with the channels of the first set, and a third set of generally parallel channels which intersect with the channels of the first and second sets and each of which is defined by a 9-membered ring of tetrahedrally coordinated atoms. The first set of 10-ring channels each has cross-sectional dimensions of about 4.8 Å by about 5.5 Å, whereas the second set of 10-ring channels each has cross-sectional dimensions of about 5.0 Å by about 5.7 Å. The third set of 9-ring channels each has cross-sectional dimensions of about 4.0 Å by about 4.9 Å.

Preferably, the zeolite employed in the process of this disclosure is ZSM-5 having a silica to alumina molar ratio of at least 250, as measured prior to any treatment of the zeolite to adjust its diffusivity.

The medium pore zeolites described above are preferred for the process of this disclosure since the size and shape of their pores favor the production of para-xylene over the other xylene isomers. However, conventional forms of these zeolites have Diffusion Parameter values in excess of the 0.1-15 sec$^{-1}$ range required for the process of this disclosure. The required diffusivity for the present catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the porous crystalline material is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups 2, 3, 4, 5, 6, 13, 14, and 15 of the Periodic Table. Most preferably, the at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier in the catalyst of this disclosure is conveniently achieved by the methods described in U.S. Pat. Nos. 4,356.338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours.

Similar techniques known in the art can be used to incorporate other modifying oxides into the catalyst of this disclosure.

Representative phosphorus-containing compounds which may be used to incorporate a phosphorus oxide modifier into the catalyst of this disclosure include derivatives of groups represented by $PX_3$, $RPX_2$, $R_2PX$, $R_3P$, $X_3PO$, $(XO)_3PO$, $(XO)_3P$, $R_3P=O$, $RP=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloroidites, $R_2PCl$, alkyl alkylphosphonochloridates. $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$. $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite. phosphorus trichloride, phosphoric acid, phenyl phosphine oxychloride, trimethylphosphate, diphenyl phosphinous acid, diphenyl phosphinic acid, diethyichlorothiophosphate, methyl acid phosphate, and other alcohol-$P_2O_5$ reaction products.

Representative boron-containing compounds which may be used to incorporate a boron oxide modifier into the catalyst of this disclosure include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylae, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of this disclosure may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e., clays, oxides, etc, function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmoillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20-200 microns.

The catalyst of this disclosure may optionally be precoked. The precoking step is preferably carried out by initially utilizing the uncoked catalyst in the toluene methylation reaction, during which coke is deposited on the catalyst surface and thereafter controlled within a desired range, typically from about 1 to about 20 wt % and preferably from about 1 to about 5 wt %, by periodic regeneration by exposure to an oxygen-containing atmosphere at an elevated temperature.

The "alpha value" refers to the acid activity of a catalyst, which is exemplified by its catalytic cracking activity. The alpha test is described in U.S. Pat. No. 3,354,078 and in *The Journal of Catalysis*, Vol. 4, pp.522-529 (1965); Vol. 6, p. 278 (1966); and Vol. 61, p. 395 (1980), each incorporated herein by reference as to that description.

Usually, the catalyst containing the porous crystalline material will have an alpha value in the range from about 0.1 to about 100, and, more preferably, in the range from about 0.5 to about 10.

The catalyst comprising the porous crystalline material can be selectivated with a selectivating agent when used in aromatics conversion, e.g., toluene disproportionation, xylenes isomerization, aromatics alkylation, light olefin conversion to aromatics, and the like. The term "selectivating agent" is used herein to indicate substances which will increase the shape-selectivity (e.g., para-selectivity) of the porous crystalline material. The catalyst can be selectivated by treating the surface of the catalyst with compounds of phosphorus and/or various metal oxides such as alkaline earth metal oxides, e.g., calcium oxide, magnesium oxide, etc. rare earth metal oxides, lanthanum oxide, and other metal oxides such as boron oxide, titania, antimony oxide, and manganese oxide. The catalyst can also be selectivated by depositing coke on the catalyst.

Furthermore, selectivation can be accomplished using organosilicon compounds. The organosilicon compounds may comprise polysiloxane including silicone and siloxanes, and a silane including disilanes and alkoxysilanes.

Organosilicon compounds include siloxanes which can be represented by the general formula:

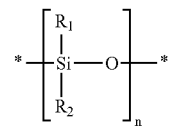

wherein $R_1$ is hydrogen, halogen, hydroxyl, alkyl, halogenated alkyl, aryl aralkyl, halogenated aralkyl, alkaryl, or halogenated alkaryl. The hydrocarbon substituents generally contain from 1 to about 10 carbon atoms, preferably methyl, ethyl, or phenyl groups. $R_2$ is selected from the same group as $R_1$, and n is an integer of at least 2 and generally in the range of 3 to about 1000. The molecular weight of the silicone compound employed is generally between about 80 to about 20,000 and preferably about 150 to about 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylphenyl silicone, methylvinyl silicone and ethylvinyl silicone. The silicone compound need not be linear but may be cyclic as for example hexamethyl cyclotrisiloxane, octamethyl cyclotetrasiloxane, hexaphenyl cyclotrisiloxane, and octaphenyl cyclotetrasiloxane. Mixtures of these compounds may also be used as well as silicones with other functional groups. Other silicon compounds, including silanes, alkoxy silanes, such as tetramethoxy silane, can also be utilized. These useful silicon-containing selectivating agents include silanes characterized by the general formula:

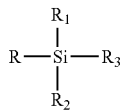

wherein R, $R_1$, $R_2$ and $R_3$ are independently selected from the group consisting of hydrogen, hydroxyl, halogen, alkyl, halogenated alkyl, alkoxy, aryl, halogenated alkaryl groups. Mixtures of these compounds can also be used.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich.

Examples of suitable carriers for the selectivating silicon compound include linear, branched, and cyclic alkane having five or more carbons. In the methods of the present invention it is preferred that the carrier be a linear, branched, or cyclic alkane having a boiling point greater than about 70° C., and most preferably containing 6 or more carbons. Optionally, mixtures of low volatility organic compounds, such as hydrocracker recycle oil, can be employed as carriers. The most preferred low volatility hydrocarbon carriers of selectivating agents are decane and dodecane.

The catalyst can be selectivated by single or multiple treatments with a liquid organosilicon compound in a liquid carrier, each treatment being followed by calcination of the treated material in an oxygen containing atmosphere. The catalyst can also be selectivated with both silica and coke.

One of the advantages of the catalyst described herein is its ease of regenerability. Thus, after the catalyst accumulates coke as it catalyzes the toluene methylation reaction, it can easily be regenerated by burning off a controlled amount of coke in a partial combustion atmosphere in a regenerator at temperatures in the range from about 400 to about 700° C. The coke loading on the catalyst may thereby be reduced or substantially eliminated in the regenerator. If it is desired to maintain a given degree of coke loading, the regeneration step may be controlled such that the regenerated catalyst returning to the toluene methylation reaction zone is coke-loaded at the desired level.

The present process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

In some embodiments, this disclosure relates to:

Paragraph 1. A process of manufacturing para-xylene, comprising:
  (a) contacting a pygas feedstock and methylating agent with a catalyst under reaction conditions to produce a product having para-xylene, wherein said product has higher para-xylene content than the para-xylene content of the pygas feedstock; and
  (c) separating said para-xylene from the product of the step (a),
  wherein said catalyst comprises a molecular sieve having a Diffusion Parameter for 2,2-dimethylbutane of about 0.1-15 $sec^{-1}$ when measured at a temperature of 120° C. and a 2,2-dimethylbutane pressure of 8 kPa-a and said pygas comprises from about 1 to about 65 wt % benzene and from about 5 to 35 wt % toluene.

Paragraph 2. The process of paragraph 1, wherein said pygas feedstock further comprises from about 1 to 15 wt % $C_8$ aromatic compounds and at least 20 wt % of said $C_8$ aromatic compounds is ethylbenzene.

Paragraph 3. The process of any preceding paragraph, wherein said catalyst is produced by a method comprising steps of:
  (1) providing a porous crystalline material having a Diffusion Parameter for 2,2-dimethylbutane in excess of 15 $sec^{-1}$ when measured at a temperature of 120° C. and a 2,2-dimethylbutane pressure of 8 kPa-a; and
  (2) contacting the material of step (1) with steam at a temperature in excess of 1000° C. to reduce the Diffusion Parameter thereof for 2,2-dimethylbutane to about 0.1-15 $sec^{-1}$ when measured at a temperature of 120° C. and a 2,2-dimethylbutane pressure of 8 kPa-a, the micropore volume of the steamed material being at least 50% of the unsteamed material.

Paragraph 4. The process of paragraph 3, wherein the porous crystalline material is combined with a source of at least one oxide modifier selected from the group consisting of oxides of elements of Groups 2, 3, 4, 5, 6, 13, 14, and 15 of the Periodic Table prior to step (2).

Paragraph 5. The process of paragraph 3 or 4, wherein the porous crystalline material is combined with a source of at least one oxide modifier selected from the group consisting of oxides of boron, magnesium, calcium, lanthanum and phosphorus prior to step (2).

Paragraph 6. The process of any one of paragraphs 3-5, wherein the porous crystalline material used in step (1) is an aluminosilicate zeolite having a Constraint Index of about 1 to 12.

Paragraph 7. The process of any one of paragraphs 3-6, wherein the catalyst contains about 0.05 to about 20 wt % of the oxide modifier based on the elemental modifier.

Paragraph 8. The process of paragraph 7, wherein said zeolite is ZSM-5 or ZSM-11.

Paragraph 9. The process of any preceding paragraph, wherein at least a portion of said para-xylene is made by a process comprising the following reactions:
  (a1) methylating at least a portion of said ethylbenzene to form polymethylated ethylbenzene;
  (a2) de-ethylating at least a portion of said polymethylated ethylbenzene to form toluene and para-xylene; and
  (a3) methylating said toluene of (a2) to form para-xylene.

Paragraph 10. The process of any preceding paragraph, wherein said pygas feedstock further comprises at least 5 wt % non-aromatic components.

Paragraph 11. The process of any preceding paragraph, wherein said pygas feedstock comprises less than 1 wt % of unsaturated non-aromatic hydrocarbons.

Paragraph 12. The process of any preceding paragraph, wherein said pygas feedstock comprises less than 10 wt % of non-aromatic hydrocarbons.

Paragraph 13. The process of any preceding paragraph, wherein said pygas feedstock comprises less than 10 wt % of $C_9$+ and less than 10 wt % of $C_5$−.

Paragraph 14. The process of any preceding paragraph, wherein said reaction conditions comprises a temperature ranging from about 500 to about 700° C., a pressure from about 100 to about 7000 kPa-a, a weight hourly space velocity ranging from about 0.5 and about 1000 $hr^{-1}$, and a molar ratio of toluene to methylating agent ranging from about 0.2 to about 20.

Paragraph 15. The process of any preceding paragraph, wherein said contacting step (a) further comprises hydrogen and/or added water such that the molar ratio of hydrogen and/or water to toluene+methylating agent in the feed is between about 0.01 and about 10.

Paragraph 16. The process of any preceding paragraph, wherein the product of the step (a) further comprises $C_5$− hydrocarbons, benzene and toluene, said process further comprises separating at least a portion of $C_5$− hydrocarbons to form a $C_5-$ hydrocarbons product, and separating at least a portion of said benzene and toluene to form a benzene/toluene product.

Paragraph 17. The process of paragraph 16, further comprising a step of recycling at least a portion of said benzene/toluene product to step (a).

Paragraph 18. The process of any preceding paragraph, wherein the product of the step (a) further comprises $C_9+$ hydrocarbons, said process further comprises separating at least a portion of $C_9+$ hydrocarbons to form a $C_9+$ product.

Paragraph 19. The process of paragraph 18, further comprising a step of providing at least a portion of said $C_9+$product to a transalkylation process.

Paragraph 20. The process of any preceding paragraph, wherein said pygas feedstock is made by steam cracking process.

Paragraph 21. The process of paragraph 20, wherein the feed to said steam cracking process comprises at least one of vacuum gas oil, atmospheric gas oil, light naphtha, full range naphtha, ethane, propane, butane, naphtha made by a process using resid feed, or any combination thereof.

Paragraph 22. The process of any preceding paragraph wherein said product of step (a) comprises ethylene and propylene.

Paragraph 23. A process of co-manufacturing light olefins and para-xylene, comprising:
  (a) contacting a pygas feedstock and methylating agent with a catalyst under reaction conditions to produce a product having said light olefins and para-xylene, wherein said product has higher para-xylene content than the para-xylene content of the pygas feedstock; and
  (d) separating said para-xylene from the product of the step (a),
  wherein said catalyst comprises a molecular sieve having a Diffusion Parameter for 2,2-dimethylbutane of about 0.1-15 $sec^{-1}$ when measured at a temperature of 120° C. and a 2,2-dimethylbutane pressure of 8 kPa-a and said pygas comprises at least 1 wt % non-aromatic components, from about 15 to about 65 wt % benzene, and from about 5 to 35 wt % toluene, wherein said light olefins comprise ethylene and propylene, and
  wherein said catalyst is produced by a method comprising steps of:
  (1) providing a porous crystalline material having a Diffusion Parameter for 2,2-dimethylbutane in excess of 15 $sec^{-1}$ when measured at a temperature of 120° C. and a 2,2-dimethylbutane pressure of 8 kPa-a; and
  (2) contacting the material of step (1) with steam at a temperature in excess of 1000° C. to reduce the Diffusion Parameter thereof for 2,2-dimethylbutane to about 0.1-15 $sec^{-1}$ when measured at a temperature of 120° C. and a 2,2-dimethylbutane pressure of 8 kPa-a, the micropore volume of the steamed material being at least 50% of the unsteamed material.

Paragraph 24. The process of paragraph 23, wherein the porous crystalline material is combined with a source of at least one oxide modifier selected from the group consisting of oxides of elements of Groups 2, 3, 4, 5, 6, 13, 14, and 15 of the Periodic Table prior to step (2) and the porous crystalline material used in step (1) is an aluminosilicate zeolite having a Constraint Index of about 1 to 12.

Paragraph 25. The process of paragraph 24, wherein said zeolite is ZSM-5 or ZSM-11.

Paragraph 26. The process of paragraph 24 or 25, wherein at least a portion of said para-xylene is made by a process comprising the following reactions:
  (a1) methylating at least a portion of said ethylbenzene to form polymethylated ethylbenzene;
  (a2) de-ethylating at least a portion of said polymethylated ethylbenzene to form toluene and para-xylene; and
  (a3) methylating said toluene of (a2) to form para-xylene; and
  wherein at least a portion of said light olefins is made by a process comprising the following reactions:
  (b1) reacting methylating agent to form light olefins;
  (b2) de-ethylating of ethylbenzene or polymethylated ethylbenzene; and
  (b3) cracking of non-aromatic compounds in said pygas feedstock.

Paragraph 27. The process of any one of paragraphs 24-26, wherein said pygas feedstock is made by steam cracking process.

Paragraph 28. The process of paragraph 27, wherein the feed to said steam cracking process comprises at least one of vacuum gas oil, atmospheric gas oil, light naphtha, full range naphtha, ethane, propane, butane, naphtha made by a process using resid feed, or any combination thereof.

Paragraph 29. A process of co-manufacturing light olefins and para-xylene, comprising:
  (a) steam cracking a feedstock comprising at least one of vacuum gas oil, atmospheric gas oil, light naphtha, full range naphtha, ethane, propane, butane, naphtha made by a process using resid feed, or any combination thereof to form a product comprising pygas and light olefins;
  (b) Separating said light olefins from said pygas;
  (c) contacting said pygas and a methylating agent with a catalyst under reaction conditions to produce a product having para-xylene, wherein said product has higher para-xylene content than the para-xylene content of the pygas feedstock; and
  (e) separating said para-xylene from the product of the step (c),
  wherein said catalyst comprises a molecular sieve having a Diffusion Parameter for 2,2-dimethylbutane of about 0.1-15 $sec^{-1}$ when measured at a temperature of 120° C. and a 2,2-dimethylbutane pressure of 8 kPa-a and said pygas comprises at least 1 wt % non-aromatic components, from about 15 to about 65 wt % benzene, and from about 5 to 35 wt % toluene, wherein said light olefins comprise ethylene and propylene, and
  wherein said catalyst is produced by a method comprising steps of:
  (1) providing a porous crystalline material having a Diffusion Parameter for 2,2-dimethylbutane in excess of 15 $sec^{-1}$ when measured at a temperature of 120° C. and a 2,2-dimethylbutane pressure of 8 kPa-a; and
  (2) contacting the material of step (1) with steam at a temperature in excess of 1000° C. to reduce the Diffusion Parameter thereof for 2,2-dimethylbutane to about 0.1-15 $sec^{-1}$ when measured at a temperature of 120° C. and a 2,2-dimethylbutane pressure of 8 kPa-a, the micropore volume of the steamed material being at least 50% of the unsteamed material.

Paragraph 30. A light olefins and para-xylene co-manufacturing system comprising:
  (a) a steam cracking unit adapted for steam cracking a hydrocarbon feedstock to light olefins and pygas;
  (b) a first separating unit adapted for separating said light olefins from said pygas;
  (c) a methylation unit adapted to methylating at least a portion of said pygas from (b) to produce a product para-xylene; and (d) a second separating unit adapted for separating said para-xylene from said product.

Paragraph 31. The system of paragraph 30 further comprising a hydroprocessing unit adapted for hydroprocessing resid feedstock to form a naphtha suitable as a feedstock for said steam cracking unit.

EXAMPLES

Example 1

A spreadsheet simulation was performed using material balance. The simulation integrated a typical resid-fining process with a methylation process and a transalkylation process. The results of the simulation are demonstrated in FIG. 1 as one embodiment of an integrated system comprising hydroprocessing, steam cracking, and methylation processes using resid as a feedstock. A resid feedstock was supplied via line 1 to a hydroprocessing/steam cracking unit 3. The hydroprocessing severity and/or the steam cracking severity were adjusted to produce 22 weight units of pygas per 100 unit of the resid feedstock. The pygas produced preferentially contains >95 wt % $C_9$– hydrocarbons. About 16 weight units of the total 22 weight units of the pygas are $C_8$– feedstock, mainly $C_8$– aromatics, and about 6 weight units of the total 22 weight units of the pygas are $C_9$+ feedstock, mainly $C_0$+ aromatics. Because the pygas was produced from a resid feedstock, the yield of the pygas from the steam cracker effluent is high as comparing with other feedstocks, such as naphtha, under similar steam cracking conditions. The pygas made from steam cracking of a resid feedstock normally has a high toluene and $C_8$ aromatics content as comparing with a pygas made from steam cracking other feedstocks, such as naphtha, under similar steam cracking conditions. The pygas produced from the hydroprocessing/steam cracking unit 3 was supplied to a first separation unit 7 via line 5. About 16 weight units of the pygas were separated as a $C_8$– feedstock and supplied to a methylation unit 11 via line 9. About 8 weight unit of methylating agent, e.g., methanol, were supplied to the methylation unit 11 via line 13. The product of the methylation unit 11 comprising light olefins, e.g., ethylene and/or propylene, para-xylene, lights, and heavies, was supplied to a second separation unit 17. The $C_7$– aromatics were separated and optionally recycled to the methylation unit 11 via line 19. About 6 weight units of $C_9$+ feedstock was separated from the pygas product at the separation unit 7 and are supplied to a transalkylation unit 23 via line 21. The product of the transalkylation unit 23 was subjected to further separation at the second separation unit 17. The $C_9$+ aromatics were separated and optionally recycled to the transalkylation unit via line 27. The lights were withdrawn from the separation unit 17 via line 29 as a lights product. The light olefins were withdrawn from the separation unit 17 via line 31 as a light olefins product. The para-xylene was withdrawn from the separation unit 17 via line 33 as a para-xylene product. The heavies were withdrawn from the separation unit 17 via line 35 as a heavies product.

It has not been reported or rendered obvious in any prior art that p-xylene can be produced from resid feedstock with a 20 wt % yield. The state of the art technology today for producing p-xylene integrates naphtha reforming with an aromatics plant. Typical p-xylene yield on naphtha feed is 35 to 40 wt %. It is surprising that naphtha can be substituted with much less costly residual oil feedstock and produce p-xylene in similar yields using a similar number of processing steps.

Example 2

A phosphorus stabilized ZSM-5 with an alpha value of 1 and 2,2 dimethylbutane Diffusion Parameter of 1 $sec^{-1}$ (measured at a temperature of 120° C. and a 2,2-dimethylbutane pressure of 8 kPa-a) was used to convert an 80 wt % methanol, 20 wt % p-ethyltoluene feedstock. The reaction was run in a fixed-bed reactor at 0.7 $hr^{-1}$ WHSV, 101.3 kPa-a pressure and a temperature of 390° C. The products of the reaction are listed in the following table.

| Name | Wt % in Product Composition |
| --- | --- |
| $C_1$-$C_4$ paraffins | 1 |
| Ethylene | 9.5 |
| Propylene | 7 |
| Butenes | 3 |
| $C_5$+ non aromatics | 2.5 |
| toluene | 0.5 |
| p-xylene | 2.5 |
| Other aromatics | 1 |
| water | 29 |
| p-ethyltoluene | 15 |
| Dimethyl ether plus methanol | 29 |

In the example, methanol conversion to hydrocarbon products is 67 wt %. P-ethyltoluene conversion is 25 wt %. The example surprisingly shows that an ethyltoluene can be converted to p-xylene and ethylene with high selectivity. Those skilled in the art will recognize that when ethylbenzene is reacted with methanol over the same catalyst, the primary product is an ethyltoluene. The example proves that ethyltoluenes are readily converted to ethylene and p-xylene. The examples prove that mixtures of ethylbenzene, toluene, and benzene will react with methanol to produce p-xylene and light olefins.

Example 3

Figure 2:
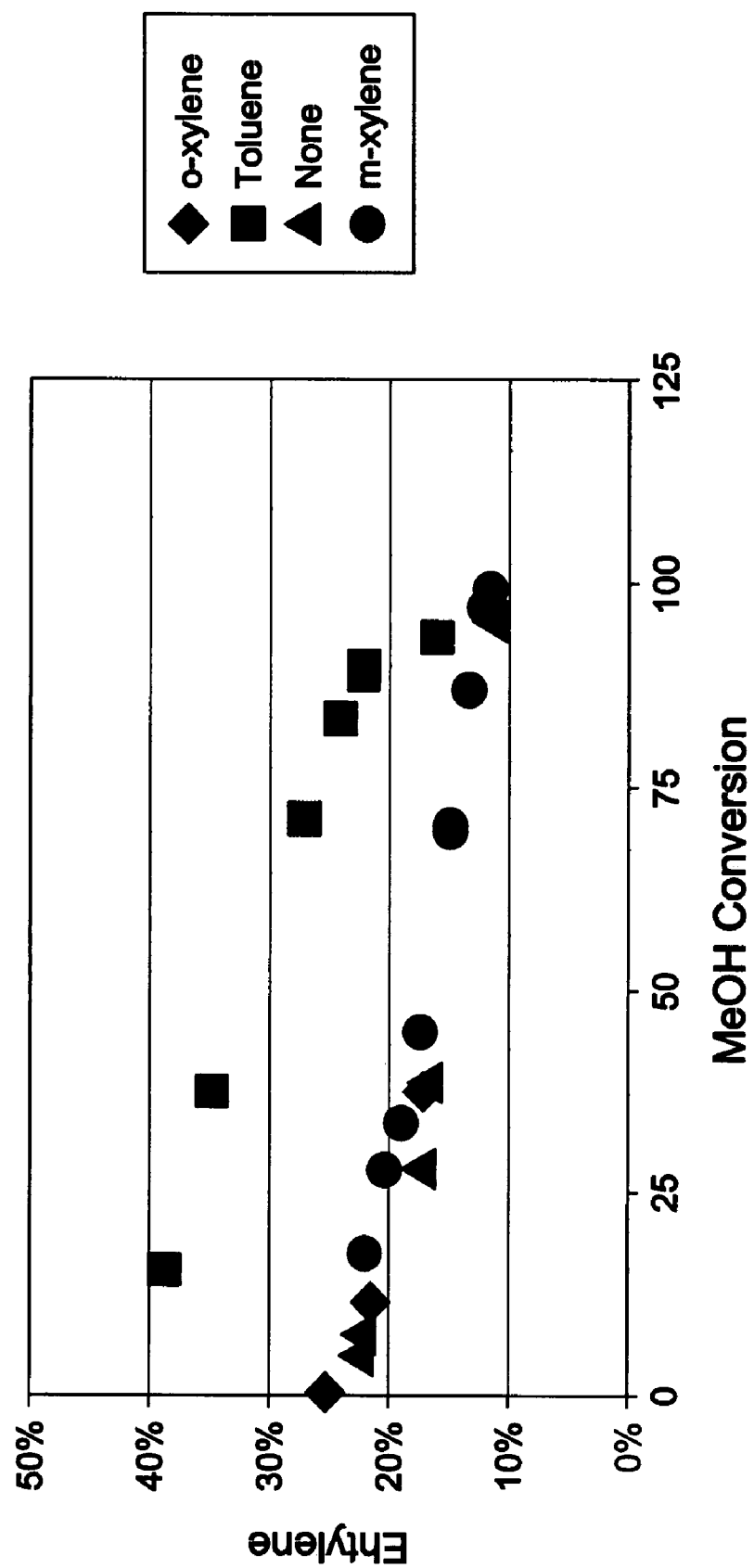
FIG. 2 plots ethylene selectivity as a function of methanol conversion for Examples 3 and 4.

A 65 wt % ZSM-5 ($SiO_2$:$Al_2O_3$ molar ratio of 450:1) catalyst had been steamed at 510° C. for 1 hour. The steamed catalyst has an alpha value of about 1, a 2,2 dimethylbutane Diffusion Parameter of about 0.5 $sec^{-1}$ (measured at a temperature of 120° C. and a 2,2-dimethylbutane pressure of 8 kPa-a), and a n-hexane sorption of 65 mg/g, was used to convert methanol at 430° C. and 101.3 kPa-a. Ethylene selectivity as a function of methanol conversion is reported in FIG. 2.

Example 4

The catalyst of example 3 was used to convert 55:1 molar mixtures of methanol and aromatic cofeeds at 430° C. and 101.3 kPa-a. Three aromatic cofeeds were used: toluene, ortho-xylene, and metaxylene. Ethylene selectivity as a function of methanol conversion is reported in FIG. 2.

Example 5

Figure 3:
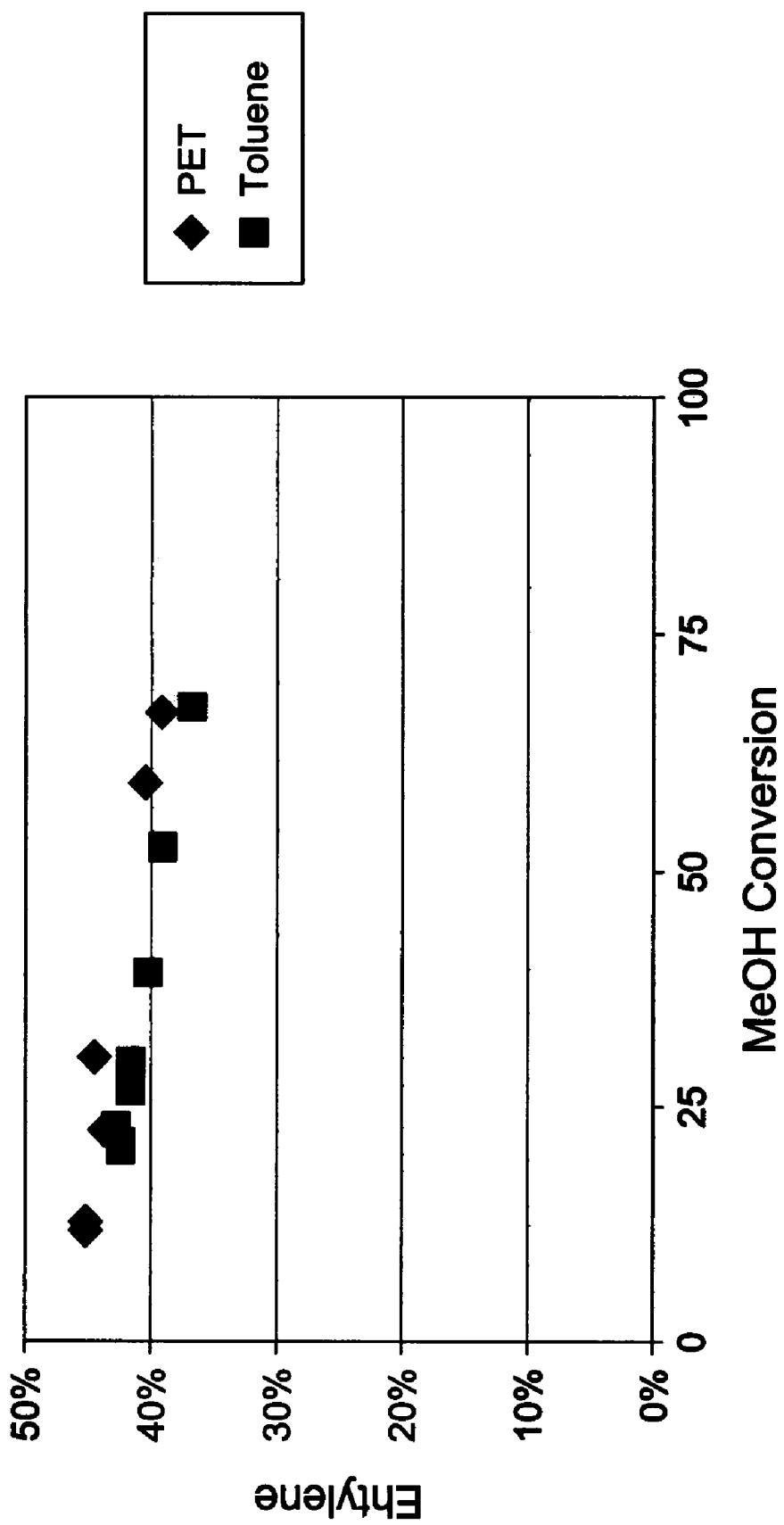
FIG. 3 plots ethylene selectivity as a function of methanol conversion for Example 5.

The catalyst of example 3 was used to convert a 12:1 molar mixture of methanol and para-ethyltoluene or toluene at 380° C. and 101.3 kPa-a. Ethylene selectivity as a function of methanol conversion is reported in FIG. 3 for both feedstocks.

Trade names used herein are indicated by a ™ symbol or ® symbol, indicating that the names may be protected by certain trademark rights, e.g., they may be registered trademarks in various jurisdictions.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

We claim:

1. A process of manufacturing para-xylene, comprising:
(a) contacting a pygas feedstock and methylating agent with a catalyst under reaction conditions to produce a product having para-xylene, wherein said product has higher para-xylene content than the para-xylene content of the pygas feedstock; and
(f) separating said para-xylene from the product of the step (a), wherein said catalyst comprises a molecular sieve having a Diffusion Parameter for 2,2-dimethylbutane of about 0.1-15 sec-1 when measured at a temperature of 120° C. and a 2,2-dimethylbutane pressure of 8 kPa-a, said pygas comprises from about 1 to about 65 wt % benzene, from about 5 to 35 wt % toluene, from about 1 to 15 wt % C8 aromatic compounds, and at least 20 wt % of said C8 aromatic compounds is ethylbenzene, wherein at least a portion of said para-xylene is made by a process comprising the following reactions:
(a1) methylating at least a portion of said ethylbenzene to form polymethylated ethylbenzene;
(a2) de-ethylating at least a portion of said polymethylated ethylbenzene to form toluene and para-xylene; and
(a3) methylating said toluene of (a2) to form para-xylene.

2. The process of claim 1, wherein said catalyst is produced by a method comprising steps of:
(1) providing a porous crystalline material having a Diffusion Parameter for 2,2-dimethylbutane in excess of 15 $sec^{-1}$ when measured at a temperature of 120° C. and a 2,2-dimethylbutane pressure of 8 kPa-a; and
(2) contacting the material of step (1) with steam at a temperature in excess of 1000° C. to reduce the Diffusion Parameter thereof for 2,2-dimethylbutane to about 0.1-15 $sec^{-1}$ when measured at a temperature of 120° C. and a 2,2-dimethylbutane pressure of 8 kPa-a, the micropore volume of the steamed material being at least 50% of the unsteamed material.

3. The process of claim 2, wherein the porous crystalline material is combined with a source of at least one oxide modifier selected from the group consisting of oxides of elements of Groups 2, 3, 4, 5, 6, 13, 14, and 15 of the Periodic Table prior to step (2).

4. The process of claim 2, wherein the porous crystalline material is combined with a source of at least one oxide modifier selected from the group consisting of oxides of boron, magnesium, calcium, lanthanum and phosphorus prior to step (2).

5. The process of claim 2, wherein the porous crystalline material used in step (1) is an aluminosilicate zeolite having a Constraint Index of about 1 to 12.

6. The process of claim 2, wherein the catalyst contains about 0.05 to about 20 wt % of the oxide modifier based on the elemental modifier.

7. The process of claim 6, wherein said molecular sieve is ZSM-5 or ZSM-11.

8. The process of claim 1, wherein said pygas feedstock further comprises at least 5 wt % non-aromatic components.

9. The process of claim 1, wherein said pygas feedstock comprises less than 1 wt % of unsaturated non-aromatic hydrocarbons.

10. The process of claim 1, wherein said pygas feedstock comprises less than 10 wt % of non-aromatic hydrocarbons.

11. The process of claim 1, wherein said pygas feedstock comprises less than 10 wt % of $C_9+$ and less than 10 wt % of $C_5-$.

12. The process of claim 1, wherein said pygas feedstock further comprises less than 2 wt % of multi-unsaturated non-aromatics.

13. The process of claim 1, wherein said pygas feedstock further comprises less than 0.01 wt % of multi-unsaturated non-aromatics.

14. The process of claim 1, wherein said reaction conditions comprises a temperature ranging from about 500 to about 700° C., a pressure from about. 100 to about 7000 kPa-a, a weight hourly space velocity ranging from about 0.5 and about 1000 $hr^{-1}$, and a molar ratio of toluene to methylating agent ranging from about 0.2 to about 20.

15. The process of claim 1, wherein said contacting step (a) further comprises hydrogen and/or added water such that the molar ratio of hydrogen and/or water to toluene+methylating agent in the feed is between about 0.01 and about 10.

16. The process of claim 1, wherein the product of the step (a) further comprises $C_5-$ hydrocarbons, benzene and toluene, said process further comprises separating at least a portion of $C_5-$ hydrocarbons to form a $C_5-$ hydrocarbons product, and separating at least a portion of said benzene and toluene to form a benzene/toluene product.

17. The process of claim 16, further comprising a step of recycling at least a portion of said benzene/toluene product to step (a).

18. The process of claim 1, wherein the product of the step (a) further comprises $C_9+$ hydrocarbons, said process further comprises separating at least a portion of $C_9+$ hydrocarbons to form a $C_9+$ product.

19. The process of claim 18, further comprising a step of providing at least a portion of said $C_9+$ product to a transalkylation process.

20. The process of claim 1, wherein said pygas feedstock is made by steam cracking process.

21. The process of claim 20, wherein the feed to said steam cracking process comprises at least one of vacuum gas oil, atmospheric gas oil, light naphtha, full range naphtha, ethane, propane, butane, naphtha made by a process using resid feed, or any combination thereof.

22. The process of claim 1, wherein said product of step (a) comprises ethylene and propylene.

23. A process of co-manufacturing light olefins and para-xylene, comprising:
(a) contacting a pygas feedstock and methylating agent with a catalyst under reaction conditions to produce a product having said light olefins and para-xylene, wherein said product has higher para-xylene content than the para-xylene content of the pygas feedstock; and (g) separating said para-xylene from the product of the step (a), wherein said catalyst comprises a molecular sieve having a Diffusion Parameter for 2,2-dimethylbutane of about 0.1-15 sec$^{-1}$ when measured at a temperature of 120° C. and a 2,2-dimethylbutane pressure of 8 kPa-a and said pygas comprises at least 1 wt % non-aromatic components, from about 15 to about 65 wt % benzene, and from about 5 to 35 wt % toluene, wherein said light olefins comprise ethylene and propylene, and wherein said catalyst is produced by a method comprising steps of:

(1) providing a porous crystalline material having a Diffusion Parameter for 2,2-dimethylbutane in excess of 15 sec$^{-1}$ when measured at a temperature of 120° C. and a 2,2-dimethylbutane pressure of 8 kPa-a; and (2) contacting the material of step (1) with steam at a temperature in excess of 1000° C. to reduce the Diffusion Parameter thereof for 2,2-dimethylbutane to about 0.1-15 sec$^{-1}$ when measured at a temperature of 120° C. and a 2,2-dimethylbutane pressure of 8 kPa-a, the micropore volume of the steamed material being at least 50% of the unsteamed material.

24. The process of claim 23, wherein the porous crystalline material is combined with a source of at least one oxide modifier selected from the group consisting of oxides of elements of Groups 2, 3, 4, 5, 6, 13, 14, and 15 of the Periodic Table prior to step (2) and the porous crystalline material used in step (1) is an aluminosilicate zeolite having a Constraint Index of about 1 to 12.

25. The process of claim 24, wherein said molecular sieve is ZSM-5 or ZSM-11.

26. The process of claim 24, wherein at least a portion of said para-xylene is made by a process comprising the following reactions:

(a1) methylating at least a portion of said ethylbenzene to form polymethylated ethylbenzene;

(a2) de-ethylating at least a portion of said polymethylated ethylbenzene to form toluene and para-xylene; and (a3) methylating said toluene of (a2) to form para-xylene; and wherein at least a portion of said light olefins is made by a process comprising the following reactions:

(b1) reacting methylating agent to form light olefins;

(b2) de-ethylating of ethylbenzene or polymethylated ethylbenzene; and (b3) cracking of non-aromatic compounds in said pygas feedstock.

27. The process of claim 23, wherein said pygas feedstock is made by steam cracking process.

28. The process of claim 27, wherein the feed to said steam cracking process comprises at least one of vacuum gas oil, atmospheric gas oil, light naphtha, full range naphtha, ethane, propane, butane, naphtha made by a process using resid feed, or any combination thereof.

29. A process of co-manufacturing light olefins and para-xylene, comprising:

(a) steam cracking a feedstock comprising at least one of vacuum gas oil, atmospheric gas oil, light naphtha, full range naphtha, ethane, propane, butane, naphtha made by a process using resid feed, or any combination thereof to form a product comprising pygas and light olefins;

(b) Separating said light olefins from said pygas;

(c) contacting said pygas and a methylating agent with a catalyst under reaction conditions to produce a product having and light olefins, wherein said product has higher para-xylene content than the para-xylene content of the pygas feedstock; and (d) separating said para-xylene from the product of the step (c), wherein said catalyst comprises a molecular sieve having a Diffusion Parameter for 2,2-dimethylbutane of about 0.1-15 sec$^{-1}$ when measured at a temperature of 120° C. and a 2,2-dimethylbutane pressure of 8 kPa-a and said pygas comprises at least 1 wt % non-aromatic components, from about 15 to about 65 wt % benzene, and from about 5 to 35 wt % toluene, wherein said light olefins comprise ethylene and propylene, and wherein said catalyst is produced by a method comprising steps of:

(1) providing a porous crystalline material having a Diffusion Parameter for 2,2-dimethylbutane in excess of 15 sec$^{-1}$ when measured at a temperature of 120° C. and a 2,2-dimethylbutane pressure of 8 kPa-a; and (2) contacting the material of step (1) with steam at a temperature in excess of 1000° C. to reduce the Diffusion Parameter thereof for 2,2-dimethylbutane to about 0.1-15 sec$^{-1}$ when measured at a temperature of 120° C. and a 2,2-dimethylbutane pressure of 8 kPa-a, the micropore volume of the steamed material being at least 50% of the unsteamed material.

\* \* \* \* \*